(12) United States Patent
Terry, Jr. et al.

(10) Patent No.: US 8,700,163 B2
(45) Date of Patent: Apr. 15, 2014

(54) CRANIAL NERVE STIMULATION FOR TREATMENT OF SUBSTANCE ADDICTION

(75) Inventors: Reese S. Terry, Jr., Houston, TX (US); Jacob Zabara, Miami Beach, FL (US)

(73) Assignees: Cyberonics, Inc., Houston, TX (US); Jacob Zabara, Miami Beach, FL (US)

( * ) Notice: Subject to any disclaimer, the term of this patent is extended or adjusted under 35 U.S.C. 154(b) by 389 days.

(21) Appl. No.: 11/118,451

(22) Filed: Apr. 29, 2005

(65) Prior Publication Data

US 2006/0200208 A1    Sep. 7, 2006

Related U.S. Application Data

(60) Provisional application No. 60/658,700, filed on Mar. 4, 2005.

(51) Int. Cl.
*A61N 1/05* (2006.01)

(52) U.S. Cl.
USPC ........................................................ 607/45

(58) Field of Classification Search
USPC .................................................. 607/58, 2, 42
See application file for complete search history.

(56) References Cited

U.S. PATENT DOCUMENTS

| | | | |
|---|---|---|---|
| 4,431,000 A | 2/1984 | Butler et al. | |
| 4,503,863 A | 3/1985 | Katims | |
| 4,541,432 A | 9/1985 | Molina-Negro et al. | |
| 4,556,064 A | 12/1985 | Pomeranz et al. | |
| 4,573,481 A | 3/1986 | Bullara | |
| 4,702,254 A | 10/1987 | Zabara | |
| 4,865,048 A * | 9/1989 | Eckerson | 607/45 |
| 4,867,164 A | 9/1989 | Zabara | |
| 4,977,895 A | 12/1990 | Tannenbaum | |
| 4,979,511 A | 12/1990 | Terry, Jr. | |
| 5,025,807 A | 6/1991 | Zabara | |
| 5,154,172 A | 10/1992 | Terry, Jr. et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,231,988 A | 8/1993 | Wernicke et al. | |
| 5,243,980 A | 9/1993 | Mehra | |
| 5,263,480 A * | 11/1993 | Wernicke et al. | 607/118 |
| 5,269,303 A | 12/1993 | Wernicke et al. | |
| 5,299,569 A | 4/1994 | Wernicke et al. | |

(Continued)

FOREIGN PATENT DOCUMENTS

| | | |
|---|---|---|
| EP | 1070518 | 1/2001 |
| EP | 1145736 | 10/2001 |

(Continued)

OTHER PUBLICATIONS

Bachman, D.S, et al., "Effects of Vagal Volleys and Serotonin on Units of Cingulate Cortex in Monkeys," Brain Research, 130, (1977), pp. 253-269.

(Continued)

*Primary Examiner* — Carl H Layno
*Assistant Examiner* — Jon Eric C Morales
(74) *Attorney, Agent, or Firm* — Saul Ewing LLP

(57) ABSTRACT

A method of treating a patient with at least one substance addiction, which comprises directly stimulating a cranial nerve, such as the vagus nerve, of a patient with an electrical pulse signal defined by a plurality of parameters to provide a therapy regimen for alleviating a symptom associated with the substance addiction.

1 Claim, 4 Drawing Sheets

(56) References Cited

U.S. PATENT DOCUMENTS

| | | | |
|---|---|---|---|
| 5,304,206 A | 4/1994 | Baker et al. | |
| 5,330,515 A | 7/1994 | Rutecki et al. | |
| 5,335,657 A | 8/1994 | Terry, Jr. et al. | |
| 5,458,625 A * | 10/1995 | Kendall | 607/46 |
| 5,514,175 A | 5/1996 | Kim et al. | |
| 5,531,778 A | 7/1996 | Maschino et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,601,617 A | 2/1997 | Loeb et al. | |
| 5,690,681 A | 11/1997 | Geddes et al. | |
| 5,690,688 A | 11/1997 | Noren et al. | |
| 5,690,691 A | 11/1997 | Chen et al. | |
| 5,700,282 A | 12/1997 | Zabara | |
| 5,702,428 A | 12/1997 | Tippey et al. | |
| 5,702,429 A | 12/1997 | King | |
| 5,707,400 A | 1/1998 | Terry, Jr. et al. | |
| 5,769,778 A | 6/1998 | Abrams et al. | |
| 5,792,210 A * | 8/1998 | Wamubu et al. | 607/58 |
| 5,792,212 A | 8/1998 | Weijand | |
| 5,814,092 A | 9/1998 | King | |
| 5,830,434 A | 11/1998 | Taylor et al. | |
| 5,836,994 A | 11/1998 | Bourgeois | |
| 5,861,014 A | 1/1999 | Familoni | |
| 5,861,022 A | 1/1999 | Hipskind | |
| 5,916,239 A | 6/1999 | Geddes et al. | |
| 5,919,216 A | 7/1999 | Houben et al. | |
| 5,928,272 A | 7/1999 | Adkins et al. | |
| 6,002,966 A | 12/1999 | Loeb et al. | |
| 6,006,134 A | 12/1999 | Hill et al. | |
| 6,044,846 A | 4/2000 | Edwards | |
| 6,073,048 A | 6/2000 | Kieval et al. | |
| 6,092,528 A | 7/2000 | Edwards | |
| 6,097,984 A | 8/2000 | Douglas | |
| 6,104,956 A | 8/2000 | Naritoku et al. | |
| 6,109,269 A | 8/2000 | Rise et al. | |
| 6,129,685 A * | 10/2000 | Howard, III | 600/585 |
| 6,132,361 A | 10/2000 | Epstein et al. | |
| 6,152,953 A | 11/2000 | Hipskind | |
| 6,188,929 B1 | 2/2001 | Giordano | |
| 6,219,580 B1 | 4/2001 | Faltys et al. | |
| 6,233,488 B1 | 5/2001 | Hess | |
| 6,259,951 B1 | 7/2001 | Kuzma et al. | |
| 6,295,472 B1 | 9/2001 | Rubinstein et al. | |
| 6,304,787 B1 | 10/2001 | Kuzma et al. | |
| 6,339,725 B1 | 1/2002 | Naritoku et al. | |
| 6,341,236 B1 | 1/2002 | Osorio et al. | |
| 6,374,140 B1 | 4/2002 | Rise | |
| 6,381,499 B1 | 4/2002 | Taylor et al. | |
| 6,425,852 B1 | 7/2002 | Epstein et al. | |
| 6,438,423 B1 | 8/2002 | Rezai et al. | |
| 6,449,512 B1 | 9/2002 | Boveja | |
| 6,463,328 B1 | 10/2002 | John | |
| 6,473,644 B1 | 10/2002 | Terry, Jr. et al. | |
| 6,505,074 B2 | 1/2003 | Boveja et al. | |
| 6,532,388 B1 | 3/2003 | Hill et al. | |
| 6,556,868 B2 | 4/2003 | Naritoku et al. | |
| 6,587,719 B1 | 7/2003 | Barrett et al. | |
| 6,587,727 B2 | 7/2003 | Osorio et al. | |
| 6,609,025 B2 | 8/2003 | Barrett et al. | |
| 6,610,713 B2 | 8/2003 | Tracey | |
| 6,622,041 B2 | 9/2003 | Terry, Jr. et al. | |
| 6,647,296 B2 | 11/2003 | Fischell et al. | |
| 6,721,603 B2 | 4/2004 | Zabara et al. | |
| 6,885,888 B2 | 4/2005 | Rezai | |
| 6,908,487 B2 | 6/2005 | Cigaina | |
| 7,209,787 B2 * | 4/2007 | DiLorenzo | 607/45 |
| 7,242,984 B2 * | 7/2007 | DiLorenzo | 607/45 |
| 2002/0116030 A1 | 8/2002 | Rezai | |
| 2002/0151939 A1 * | 10/2002 | Rezai | 607/40 |
| 2003/0055457 A1 | 3/2003 | MacDonald | |
| 2003/0208212 A1 | 11/2003 | Cigaina | |
| 2003/0236558 A1 * | 12/2003 | Whitehurst et al. | 607/45 |
| 2004/0015205 A1 * | 1/2004 | Whitehurst et al. | 607/48 |
| 2004/0167583 A1 | 8/2004 | Knudson et al. | |
| 2004/0167587 A1 | 8/2004 | Thompson | |
| 2004/0172085 A1 | 9/2004 | Knudson et al. | |
| 2004/0172088 A1 | 9/2004 | Knudson et al. | |
| 2004/0172094 A1 | 9/2004 | Cohen et al. | |
| 2004/0176812 A1 | 9/2004 | Knudson et al. | |
| 2004/0210270 A1 | 10/2004 | Erickson | |
| 2004/0249416 A1 | 12/2004 | Yun et al. | |
| 2005/0010262 A1 | 1/2005 | Rezai et al. | |
| 2005/0021092 A1 | 1/2005 | Yun et al. | |
| 2005/0038484 A1 * | 2/2005 | Knudson et al. | 607/40 |
| 2005/0049655 A1 | 3/2005 | Boveja et al. | |
| 2005/0060007 A1 | 3/2005 | Goetz | |
| 2005/0060008 A1 | 3/2005 | Goetz | |
| 2005/0060009 A1 | 3/2005 | Goetz | |
| 2005/0060010 A1 | 3/2005 | Goetz | |
| 2005/0065562 A1 | 3/2005 | Rezai | |
| 2005/0065573 A1 | 3/2005 | Rezai | |
| 2005/0065575 A1 | 3/2005 | Dobak | |
| 2005/0075681 A1 | 4/2005 | Rezai et al. | |
| 2005/0075701 A1 | 4/2005 | Shafer | |
| 2005/0131485 A1 | 6/2005 | Knudson et al. | |
| 2005/0131486 A1 | 6/2005 | Boveja et al. | |
| 2005/0131506 A1 | 6/2005 | Rezai et al. | |
| 2005/0192644 A1 | 9/2005 | Boveja et al. | |
| 2006/0020292 A1 | 1/2006 | Goetz et al. | |

FOREIGN PATENT DOCUMENTS

| | | |
|---|---|---|
| GB | 2079610 | 1/1982 |
| WO | 9302744 | 2/1993 |
| WO | 2004036377 A2 | 4/2004 |
| WO | 2005007120 A2 | 1/2005 |
| WO | 2005028026 A1 | 3/2005 |

OTHER PUBLICATIONS

Bohning, D.E. et al., "Feasibility of Vagus Nerve Stimulation-Synchronized Blood Oxygenation Level-Dependent Functional MRI," Investigative Radiology, vol. 36, No. 8, (Aug. 2001), pp. 470-479.

Clark, K.B., et al., "Posttraining Electrical Stimulation of Vagal Afferents With Concomitant Vagal Efferetn Inactivation Enhances Memory Storage Processes in the Rat," Neurobiology of Learning and Memory 70, Article No. NL983863, (1998) pp. 364-373.

DeGiorgio, Christopher M. et al., "Vagus Nerve Stimulation: Analysis of Device Parameters in 154 Patients During the Long-Term XE5 Study," Epilepsia, vol. 42, No. 8, 2001, pp. 1017-1020.

Dodrill, Carl B. et al., "Effects of Vagal Nerve Stimulation on Cognition and Quality of Life in Epilepsy," Epilepsy & Behavior, vol. 2, 2001, pp. 46-53.

George, Mark S. et al., "Open Trial of VNS Therapy in Severe Anxiety Disorders," 156th American Psychiatric Association Annual Meeting, May 17-22, 2003, San Francisco, California, 1 page.

Hallowitz, R.A., et al., "Effects of Vagal Volleys on Units of Intralaminar and Juxtalaminar Thalamic Nuclei in Monkeys," Brain Research, 130, (1977), pp. 271-286.

Henry, Thomas R. et al., "Brain Blood Flow Alterations Induced by Therapeutic Vagus Nerve Stimulation in Partial Epilepsy: I. Acute Effects At High and Low Levels of Stimulation," Epilepsia, vol. 39, No. 9, 1998, pp. 983-990.

Henry, Thomas R., "Therapeutic Mechanisms of Vagus Nerve Stimulation," Neurology, vol. 59, Suppl. 4, Sep. 2002, pp. S3-S14.

Kling, Michael A., et al., "Effects of Short-Term Vagus Nerve Stimulation (VNS) on FOS Expression in Rat Brain Nuclei," 58th Annual Scientific Convention of the Society of Biological Psychiatry, May 15-17, 2003, San Francisco, California, 1 page.

Klapper, Jack A. et al., "VNA Therapy Shows Potential Benefit in Patients With Migraine and Chronic Daily Headache After 3 to 6 Months of Treatment (Preliminary Results)," 45th Annual Scientific Meeting of the American Headache Society, Jun. 19-22, 2003, Chicago, Illinois, 1 page.

Koo, Betty, "EEG Changes With Vagus Nerve Stimulation," Journal of Clinical Neurophysiology, vol. 18, No. 5, (Sep. 2001), pp. 434-441.

Lockard, J.S., et al., "Feasibility and Safety of Vagal Stimulation in Monkey Model," Epilepsia, 31, (Suppl.2), (1990), pp. S20-S26.

(56) References Cited

OTHER PUBLICATIONS

Schacter, Steven C., et al., "Vagus Nerve Stimulation," Epilepsia, vol. 39, No. 7, 1998, pp. 677-686.

Tatum, IV, W.O. et al., "Ventricular Asystole During Vagus Nerve Stimulation for Epilepsy in Humans," Neurology, vol. 52, 1999, pp. 1267-1269.

Tatum, IV, W.O. et al., "Vagus Nerve Stimulation and Drug Reduction," Neurology, vol. 56, No. 4, Feb. 2001, pp. 561-563.

Terry, R.S., et al., "The Implantable Neurocybernetic Prosthesis System," Pacing and Clinical Electrophysiology, vol. 14, No. 1, (Jan. 1991), pp. 86-93.

Tubbs, R. Shane et al., "Left-Sided Vagus Nerve Stimulation Decreases Intracranial Pressure Without Resultant Bradycardia in the Pig: A Potential Therapeutic Modality for Humans," Child's Nervous System, Springer-Verlag, 2004, pp. 1-6.

Valdes-Cruz, Alejandro et al., "Chronic Stimulation of the Cat Vagus Nerve Effect on Sleep and Behavior," Progress in Neuro-Psychopharmacology & Biological Psychiatry, No. 26, 2002, pp. 113-118.

Vonck, K., et al., "The Mechanism of Action of Vagus Nerve Stimulation for Refractory Epilepsy," Journal of Neurophysiology, vol. 18, No. 5, (Sep. 2001), pp. 394-401.

Ward, Hebert et al., "Treatment-Refractory Obsessive-Compulsive Disorder: Potential Benefit of VNS Therapy," 23rd Annual Conference of the Anxiety Disorders Association of America, Mar. 27-30, 2003, Toronto, Canada, 1 page.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

Zabara, J., et al., "Inhibition of Experimental Seizures in Canines by Repetitive Vagal Stimulation," Epilepsia, 33(6), (1992), pp. 1005-1012.

\* cited by examiner

CRANIAL NERVE STIMULATION FOR TREATMENT OF SUBSTANCE ADDICTION

CROSS-REFERENCE TO RELATED APPLICATION

This application claims priority to provisional U.S. patent Application Ser. No. 60/658,700, filed Mar. 4, 2005, which is hereby incorporated herein in its entirety.

FIELD OF THE INVENTION

The present invention relates generally to methods and an apparatus for treating or controlling substance addictions by direct application of modulating electrical signals to a selected nerve or nerve bundle of the patient, and more particularly to techniques for treating patients with these addictions by application of such signals to the vagus nerve or other suitable cranial nerve, either alone or in combination, using an implantable neurostimulator. Specifically, the invention is directed toward treating the symptoms of substance addiction (e.g., cravings, withdrawal symptoms) by selective modulation of vagus nerve activity.

BACKGROUND

Substance addiction (e.g., drug addiction, alcohol addiction) is an illness. The path to addiction generally begins with the voluntary use of one or more controlled substances, such as narcotics, barbiturates, methamphetamines, alcohol, nicotine, and any of a variety of other such controlled substances. Over time, with extended use of the controlled substance(s), the voluntary ability to abstain from the controlled substance(s) is compromised due to the effects of prolonged use on brain function, and thus on behavior. As such, substance addiction generally is characterized by compulsive substance craving, seeking and use that persists even in the face of negative consequences. The cravings may represent changes in the underlying neurobiology of the patient which likely must be addressed in a meaningful way if recovery is to be obtained. Substance addiction is also characterized in many cases by withdrawal symptoms, which for some substances are life threatening (e.g., alcohol, barbiturates) and in others can result in substantial morbidity (which may include nausea, vomiting, fever, dizziness, and profuse sweating), distress, and decreased ability to obtain recovery.

For example, alcoholism, also known as alcohol dependence, is one such substance addiction. Alcoholism is primarily characterized by four symptoms, which include cravings, loss of control, physical dependence and tolerance. These symptoms also may characterize addictions to other controlled substances. The craving for alcohol, as well as other controlled substances, often is as strong as the need for food or water. Thus, an alcoholic may continue to drink despite serious family, health and/or legal ramifications.

Although alcoholism and other substance addictions generally cannot be cured, they can be treated. With treatment, many addicts are able to stop abusing a particular controlled substance and remain sober. However, treatment is not always effective. Many recovering addicts are unable to persistently resist cravings and other withdrawal symptoms indefinitely. Thus, some addicts have long periods of sobriety intermingled with bouts of relapse. Still others are unable to cease substance abuse for any appreciable length of time. Accordingly, a technique for reducing or eliminating the occurrence or severity of such cravings and withdrawal symptoms, thereby enabling the addict to abstain from substance abuse, is desirable.

Substance related disorders are thought to be due to vulnerabilities or imbalances within certain neural systems within the brain, possibly on multiple levels. For example, the neural systems underlying reward, reinforcement, compulsions (repetitive, driven behaviors), cravings, etc. may all be involved. Different substance related disorders may be more correlated with one system or brain structure over another at different stages, for instance:

- the mesolimbic dopamine system is strongly associated with stimulants and cocaine
- the locus coeruleus is strongly associated with opioid dependence
- the basal ganglia is strongly associated compulsive behaviors
- the orbitofrontal cortex is strongly associated with risk taking behavior
- the amygdala is strongly associated with cue-induced relapse
- the prefrontal cortex is strongly associated with stress-induced relapse.

The "extended amygdala" is a concept that links many of the recent developments in understanding the neurobiology of drug reward, bridging work done among separate disorders. This is a brain area (bed nucleus of the stria terminalis, central medial amygdala, medial nucleus accumbens, and the sublenticular substantia inominata) that is strongly associated with determining the emotional salience of relevant stimuli and is probably a "final common pathway" for the neurobiology of substance related disorders.

Stimulation of the vagus affects many of the brain areas known to be involved in the neurobiology of substance related disorders, including fairly direct projections to the amygdala, locus coeruleus, orbitofrontal cortex, and basal ganglia. Furthermore, it indirectly affects the "extended amygdala" in ways that might restore the inherent imbalance of that system in individuals who suffer from a substance related disorder. This might allow such individuals to simultaneously lessen the compulsive and risky behaviors associated with substance related disorders as well as increase the positive motivational aspects of behavior necessary to break the addictive cycle.

SUMMARY

The substance addictions described above may be treated by a method for treating substance addictions using stimulation of a suitable cranial nerve, preferably the vagus nerve. In one embodiment, the method comprises applying an electrical signal to a vagus nerve of the patient to alleviate a symptom of the substance addiction. The method preferably comprises surgically contacting an electrode to a vagus nerve of the patient to deliver the electrical signal directly to the vagus nerve. The electrical signal is preferably a pulsed electrical signal, and is preferably sufficient to induce afferent and/or efferent action potentials on the vagus nerve of the patient. Electrical signals intended to block native signals on the vagus nerve of the patient, however, are also within the scope of the invention.

A pulse generator may be coupled to the electrodes to generate the electrical signal for delivery to the vagus nerve. The pulse generator may be programmed to define the electrical signal in terms of a number of parameters including the current amplitude, frequency, pulse width, on-time and off-time. A healthcare provider may program the pulse generator with parameters selected to alleviate or reduce one or more symptom associated with the substance addiction. Methods of the present invention may treat substance addictions including, without limitation, cocaine addiction, alcohol addiction (alcoholism), addiction to opioids (e.g., heroin, morphine, methadone and oxycodone), sedative, hypnotic or anxiolytic-related disorders (e.g., barbiturates and benzodiazepines), hallucinogen related disorders, cannabis related disorders, amphetamine related disorders, nicotine related disorders, inhalant related disorders, phencyclidine related disorders, and polysubstance abuse disorders.

As previously noted, most substance addictions cannot be cured, and recovering addicts remain indefinitely subject to relapse. Accordingly, methods of the invention may also include treating the patient in an acute treatment period by applying a first electrical signal to a cranial nerve of the patient, and treating the patient in a chronic treatment period by applying a second electrical signal, different from the first signal, to the cranial nerve. The acute treatment period could range from a period of weeks to several months, with the chronic period extending indefinitely. The first electrical signal is preferably a signal intended at reducing immediate, uncontrollable cravings of the patient for the substance, and/or reducing or ameliorating a withdrawal symptom in the acute treatment period, and the second electrical signal is preferably provided to assist the patient in maintaining voluntary abstention from the addictive substance in the chronic treatment period. The patient may also be able to activate, by manual means such as a magnet, a treatment algorithm to provide immediate intervention in reducing substance cravings.

In another embodiment, the method comprises providing a pulse generator and an electrode, implanting the pulse generator in the patient's body, directly contacting the electrode to a cranial nerve of the patient (preferably a vagus nerve), coupling the pulse generator to the electrode, generating a pulsed electrical signal with the pulse generator, and applying the pulsed electrical signal to the electrode to alleviate a symptom of a substance addiction. The method may also comprise programming the pulse generator with an external controller to define one or more parameters of the pulsed electrical signal including current amplitude, frequency, pulse width, on-time and off-time. The pulse generator is preferably directly coupled to the electrode via a lead, although electromagnetic inductive coupling and RF signal coupling may also be employed.

In preferred methods of the present invention, the electrical signal is applied to the vagus nerve. In alternative embodiments, the electrical signal may be applied to the trigeminal or glossopharyngeal nerves, or a combination of the vagus, trigeminal, and glossopharyngeal nerves. Where the electrical signal is applied to the vagus nerve, it is preferably provided at a location in the neck area of the patient (i.e., the cervical vagus). In an alternative embodiment, the electrode may be coupled to the vagus nerve at a location slightly above or below the patient's diaphragm.

In embodiments where the electrical signal is applied to the trigeminal and/or glossopharyngeal nerves, the electrical signal may be delivered to these nerves by an electrode in direct contact with the nerve or by an external electrode coupled to the skin of the patient, and delivering an electrical signal to the nerve indirectly (i.e., transcutaneously across the skin and to the nerve). External electrodes may be more convenient for trigeminal and glossopharyngeal nerve stimulation because direct attachment to these nerves may be surgically difficult. Where stimulation of the vagus nerve is provided in conjunction with trigeminal and/or glossopharyngeal nerve stimulation, the stimulation is preferably delivered to the vagus nerve by direct contact.

Other types of indirect stimulation may also be provided in certain embodiments of the invention. In one alternative embodiment, the invention comprises providing noninvasive magnetic stimulation to a neural structure in the brain of the patient to treat the substance addiction. In a particular alternative embodiment, the invention may comprise providing transcranial magnetic stimulation (TMS) to the patient's brain to treat the substance addiction. In more preferred alternative embodiments, TMS and cranial nerve stimulation is provided to the patient to alleviate a symptom of the disorder. In a particularly preferred alternative embodiment, TMS and vagus nerve stimulation are both provided to the patient to alleviate the substance addiction.

In a further embodiment, the invention comprises a method of treating a patient suffering from substance addiction by stimulating a selected cranial nerve of the patient with an electrical signal applied to induce afferent action potentials traveling up the nerve toward the brain.

In another aspect, the invention comprises neurostimulation systems for providing electrical stimulation of a cranial nerve sufficient to induce afferent action potentials on the nerve and alleviate at least one symptom of the substance addiction. Systems of the invention comprise a an electrode directly contacting a cranial nerve, a pulse generator coupled to the electrode, and a controller comprising a treatment algorithm for causing the pulse generator to generate a pulsed electrical signal and to apply the signal to the cranial nerve via the electrode, to alleviate symptoms associated with the substance addiction.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
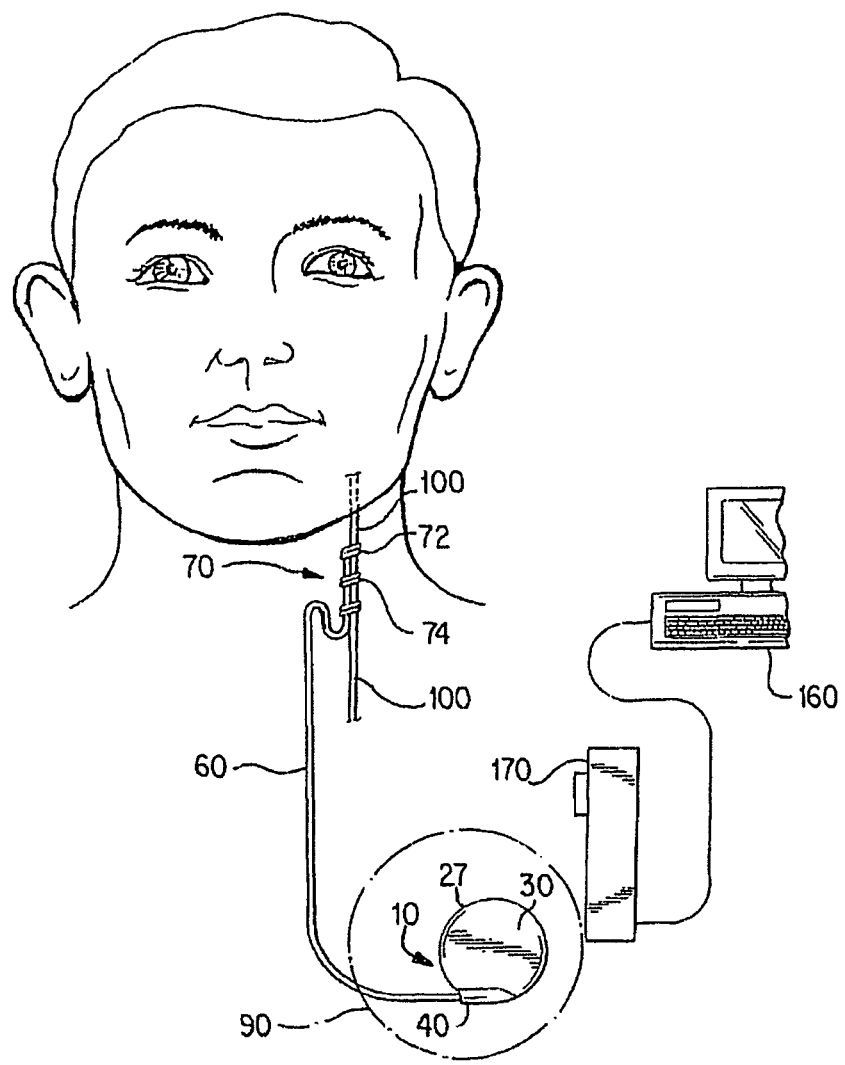
FIG. 1 is a simplified partial front view of a patient having an implanted neurostimulator for generating an electrical signal which is applied directly to the patient's left vagus nerve in the neck region via an implanted lead/nerve electrode system, with an external programming system.

Certain terms are used throughout the following description and claims to refer to particular system components. As one skilled in the art will appreciate, components may be referred to by different names. This document does not intend to distinguish between components that differ in name but not function. In the following discussion and in the claims, the terms "including" and "comprising" are used in an open-ended fashion, and thus should be interpreted to mean "including, but not limited to." Also, the term "couple" or "couples" is intended to mean either an indirect or direct electrical connection. Thus, if a first device couples to a second device, that connection may be through a direct electrical connection, or through an indirect electrical connection via other devices and connections. "Direct contact," "direct attachment" or providing a "direct coupling" implies that a surface of a first element contacts the surface of a second element with no substantial attenuating medium therebetween, although the presence of substances such as body fluids normally present throughout the body do not vitiate direct contact.

Also, the term "substance," for example as used in "substance abuse," "substance addiction," or otherwise, is intended to encompass a variety of addictive substances, such as narcotics/opiates (e.g., heroin, morphine), stimulants (e.g., amphetamine, cocaine, methamphetamine, ephedrine), sedative-hypnotics (e.g., barbiturates, benzodiazepines, ether, nitrous oxide), anabolic steroids, nitrites, alcohol, nicotine, and illicit drugs in general. Finally, all patents and patent applications specifically referred to herein are hereby specifically incorporated by reference in the present application.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Cranial nerve stimulation has been used successfully to treat a number of diseases and conditions involving brain function, including epilepsy and other movement disorders, depression and other neuropsychiatric disorders, dementia, coma, migraine headaches, obesity and eating disorders (including compulsive overeating, anorexia nervosa and bulimia nervosa), sleep disorders, cardiac conditions such as congestive heart failure and atrial fibrillation, hypertension, endocrine disorders including diabetes and hypoglycemia, pain, and other disorders. See, e.g., U.S. Pat. Nos. 4,867,164, 5,299,569, 5,269,303, 5,571,150, 5,215,086, 5,188,104, 5,263,480, 6,587,719, 6,609,025, 5,335,657, 6,622,041, 5,916,239, 5,707,400, 5,231,988, 5,330,515. Despite the recognition that cranial nerve stimulation may be an appropriate treatment for the foregoing conditions, the fact that detailed neural pathways for many (if not all cranial nerves) remain unknown makes predictions of efficacy for any given condition or disorder impossible. Even if such pathways were known, moreover, the precise stimulation parameters that would energize particular pathways that affect the particular disorder likewise cannot be predicted. Accordingly, cranial nerve stimulation has not heretofore been deemed appropriate for use in treating addiction disorder.

Disclosed herein is a method that treats substance addictions using stimulation of a suitable cranial nerve, especially the $10^{th}$ cranial nerve, also known as the vagus nerve. Other cranial nerves may be stimulated instead of or in addition to the vagus nerve, including the trigeminal nerve ($5^{th}$ cranial nerve) and the glossopharyngeal nerve ($9^{th}$ cranial nerve), although stimulation may also be applied to other cranial nerves. A generally suitable form of neurostimulator for use in the apparatus and method of the present invention is disclosed, for example, in U.S. Pat. No. 5,154,172, assigned to the same assignee as the instant application (the device also referred to from time to time herein as a NeuroCybemetic Prosthesis or NCP device (NCP is a registered trademark of Cyberonics, Inc., Houston, Tex., the assignee of the present invention). Certain parameters of the electrical stimuli generated by the neurostimulator are programmable, preferably by means of an external programmer (not shown) in a conventional manner for implantable electrical medical devices.

Figure 4:
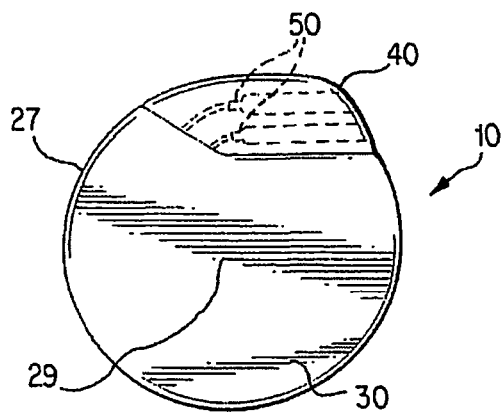
FIG. 4 is a front view of an implantable pulse generator suitable for use in the present invention, showing the header and electrical connectors for coupling the device to a lead/electrode assembly.

FIG. 1 illustrates a neurostimulator system for stimulating the vagus nerve 100 of a patient. Pulse generator 10 is provided with a main body 30 comprising a case or shell 27 with a header 40 having one or more electrical connectors 50 (FIG. 4) for connecting to leads 60. The generator 10 is implanted in the patient's chest in a pocket or cavity formed by the implanting surgeon below the skin (indicated by a dotted line 90), similar to the implantation procedure for a pacemaker pulse generator. A stimulating nerve electrode assembly 70, preferably comprising an electrode pair 72, 74, is conductively connected to the distal end of an insulated electrically conductive lead assembly 60, which preferably comprises a pair of lead wires (one wire for each electrode of an electrode pair). Each lead wire in lead assembly 60 is attached at its proximal end to a connector 50 on case 27. The electrode assembly 70 is surgically coupled to a vagus nerve 100 in the patient's neck (FIG. 1) or near the diaphragm (FIGS. 2A-2D).

Figure 3:
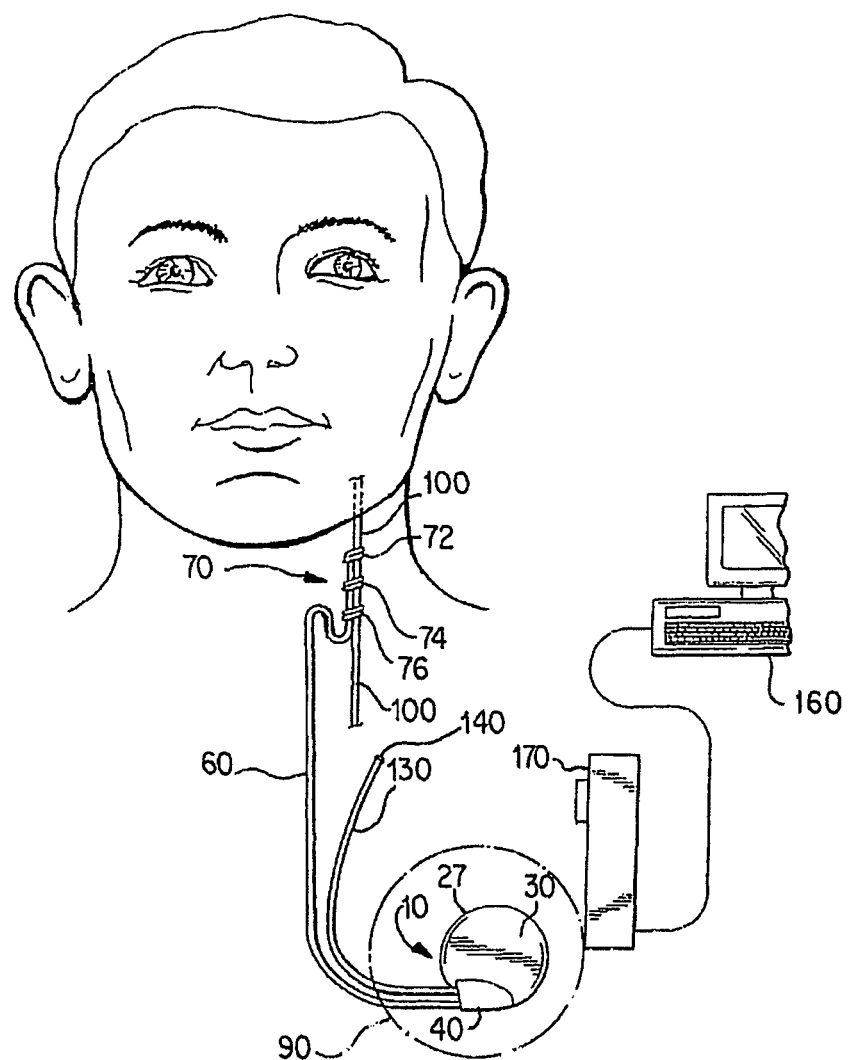
FIG. 3 is a simplified partial front view of a patient in which an implanted neurostimulator is coupled to an electrode for providing direct vagus nerve stimulation to a patient; a sensor for sensing a body parameter and triggering therapeutic vagus nerve stimulation is also included.
Figure 5:
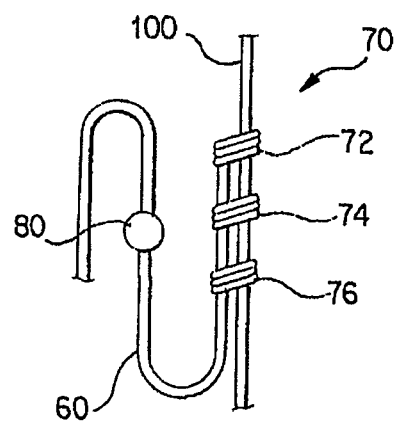
FIG. 5 illustrates a lead and electrodes suitable for use in the present invention attached to a vagus nerve of a patient.

Electrode assembly 70 preferably comprises a bipolar stimulating electrode pair (FIG. 5), such as the electrode pair described in U.S. Pat. No. 4,573,481 issued Mar. 4, 1986 to Bullara. Persons of skill in the art will appreciate that many electrode designs could be used in the present invention. The two electrodes preferably directly contact the vagus nerve. As shown in FIGS. 1, 3 and 5, in a particular embodiment a spiral-shaped electrode is wrapped about the vagus nerve, and the electrode assembly 70 is preferably secured to the nerve 100 by a spiral anchoring tether 76 (FIG. 5) such as that disclosed in U.S. Pat. No. 4,979,511 issued Dec. 25, 1990 to Reese S. Terry, Jr. and assigned to the same assignee as the instant application. Lead assembly 60 is secured, while retaining the ability to flex with movement of the chest and neck, by a suture connection 80 to nearby tissue. While the electrodes 72, 74 of electrode assembly 70 are shown in the preferred embodiment of directly contacting the vagus nerve 100, it is to be understood that embodiments in which the electrodes do not directly contact the nerve are also within the scope of the present invention, so long as the electrodes are electrically coupled to the vagus nerve 100.

Electrode assembly 70 preferably conforms to the shape of the nerve, providing a low stimulation threshold by allowing a large stimulation contact area with the nerve. In one embodiment, the electrode assembly 70 comprises two electrode ribbons (not shown), of a conductive material such as platinum, iridium, platinum-iridium alloys, and/or oxides of the foregoing. The electrode ribbons preferably are individually bonded to an inside surface of an elastomeric body portion of the two spiral electrodes 72 and 74 (FIG. 6), which may comprise two spiral loops of a three-loop helical assembly.

Lead assembly 60 may comprise two distinct lead wires or a coaxial cable whose two conductive elements are respectively coupled to one of the conductive electrode ribbons 72 and 74. One suitable method of coupling the lead wires or cable to the electrodes comprises a spacer assembly such as that disclosed in U.S. Pat. No. 5,531,778, although other known coupling techniques may be used. The elastomeric body portion of each loop is preferably composed of silicone rubber, and the third loop 76 (which typically has no electrode) acts as the anchoring tether for the electrode assembly 70. Although FIG. 1 illustrates a system for stimulating only the left vagus nerve in the neck (cervical) area, in alternative embodiments the stimulation signal may be applied to the right cervical vagus nerve in addition to or instead of the left vagus nerve. In such embodiments, lead and electrode assemblies substantially as discussed above may be coupled to the same or a different generator. FIG. 1 also illustrates an external programming system capable of wireless (i.e., radio frequency) communication with the pulse generator 10, which may be used to program a therapeutic electrical signal in the pulse generator. The external programming system comprises a wand 170 having an RF transmitter and receiver, and a computer 160, which in preferred embodiments comprises a handheld computer operable by a healthcare provider. Wand 170 communicates with a receiver and transmitter in pulse generator 10, and may be used to receive data from or transmit data to the pulse generator 10. Other communications systems, for example communications systems without a wand and operating in the recently established medical implant communication service (MICS) band at 402-405 MHz, may also be used.

Figure 2A:
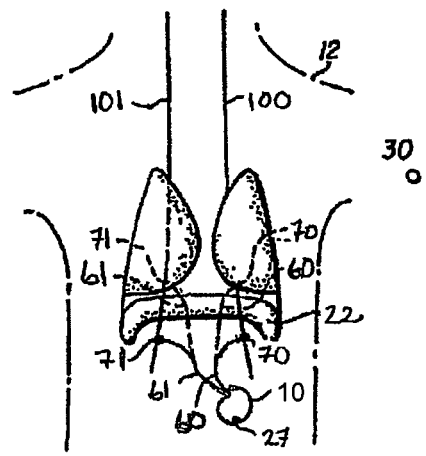
FIGS. 2A-2D are simplified partial front views of a patient having one or more implanted neurostimulators for generating and applying an electrical signal, directly or indirectly, to one or both of the left and right branches of the vagus nerve in a near-diaphragmatic location.

FIGS. 2A-2D illustrate alternative methods of stimulating the left and/or right vagus nerve branches 100, 101 near the diaphragm 22 of a patient 12. Referring to FIG. 2A, the pulse generator 10 (which may be referred to herein as stimulus generator, signal generator, neurostimulator, or simply the device), is implanted in a patient 12 in the abdominal region, for example, via a left laparotomy incision. For direct bilateral stimulation of the left and right vagus nerves, a first electrode assembly 70 (comprising electrodes 72, 74, see FIG. 1) at the distal end of lead assembly 60 is directly coupled to the left vagus nerve 100 at a location below the diaphragm 22. The proximal end of the lead 60 is electrically connected to the neurostimulator 10. A similar electrode pair 73, 75 (not shown) on a second electrode assembly 71 at the distal end of a second lead assembly 61 is coupled to the right vagus nerve 101 at a sub-diaphragmatic location, and the proximal end of lead 61 is likewise electrically connected to neurostimulator 10. The lead-electrode may be of a standard bipolar lead nerve electrode type available from Cyberonics, Inc. Although a sub-diaphragmatic electrode attachment is shown in most embodiments of FIGS. 2A-2D, an alternative embodiment in which the electrode assemblies 70, 71 are coupled to the left and right vagus nerves above the diaphragm (i.e., supra-diaphragmatically) is shown by in phantom lining and numbering (60, 70, 61, and 71). Both supra-diaphragmatic and sub-diaphragmatic locations are encompassed within the term "near-diaphragmatic," and where the latter term is used either location is intended.

Figure 2B:
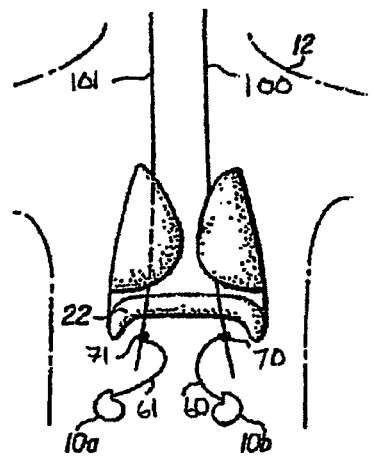
Figure 2C:
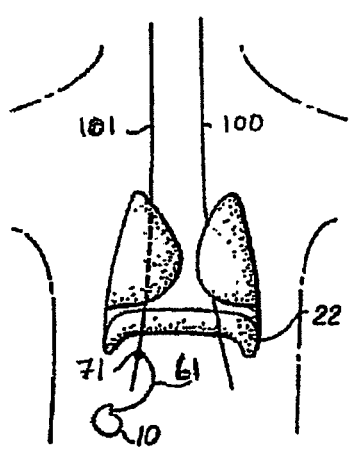
Figure 2D:
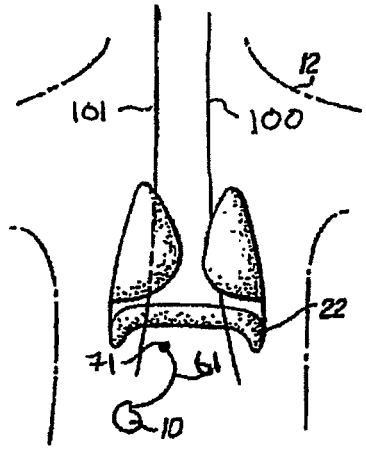

FIGS. 2B-2D illustrate alternative embodiments of near-diaphragmatic vagus nerve stimulation systems. As illustrated in FIG. 2B, each lead/electrode assembly may be coupled to a separate pulse generator 10a, 10b for stimulating the left and right vagus nerve branches, in contradistinction to the use of a single pulse generator 10 shown in FIGS. 1 and 2A. Use of multiple generators may extend the time between replacement of the generators by reducing the power drain for bilateral stimulation. In FIG. 2C, a system is shown for the direct, unilateral stimulation of the right vagus nerve 101, with an electrode assembly 71 attached to the vagus nerve 101 at the distal end of lead 61, which is coupled at its proximal end to pulse generator 10. Finally, in FIG. 2D, a system is provided with an electrode 71 that is not in contact with the right vagus nerve 101, but which nevertheless retains an electrical coupling to the nerve sufficient, which energized by the electrical pulses from the pulse generator 10, to generate afferent action potentials on the nerve 101.

It will be understood that the overall device generally is required to be approved or sanctioned by government authority for marketing as a medical device implantable in a patient together with electrode means to treat the addiction by stimulation of a selected cranial nerve or nerves (e.g., the vagus nerve) of the patient. Where vagus nerve stimulation is included, the treatment is performed using a predetermined sequence of electrical pulses generated by the pulse generator and applied to the selected cranial nerve at a cervical (neck), near-diaphragmatic, or other location on the vagus nerve, for alleviating symptoms of the substance addiction in the patient. Other cranial nerves will typically involve coupling the electrode at a location in the patient's head or neck. As previously indicated, the electrical pulses also may be applied to the selected cranial nerve at any other suitable location.

Returning to FIG. 1, neurostimulator 10 generates electrical stimuli in the form of electrical pulses according to one or more programmed parameters for stimulation of the vagus nerve. Typically, the stimulation parameters include pulse current, pulse width, frequency, and on-time or off-time. A table of ranges for each of these stimulation parameters is provided in Table 1. Without being bound by theory, it is believed that cranial nerve stimulation for successfully treating addictive disorders requires stimulation of a greater magnitude than that used for successful treatment of epilepsy and depression, two disorders that have been widely studied. Accordingly, in one embodiment of the present invention, methods of treating addictive disorders will embody at least one stimulation parameter having a relatively high magnitude. The parameter may comprise current. However, the maximum amplitude of the current should be adjusted accordingly until an absence of retching is observed and the patient does not experience pain, with a suitable safety margin. While the retching threshold can approach 6.0 mamp, current more typically ranges from 0.5 to 3.0 mamp. In one embodiment, a current of 1.5 mamp is used. The retching threshold may change noticeably with time over a course of days after implantation, so the level should be checked especially in the first few days after implantation to determine whether any adjustment is necessary to maintain an effective regimen.

TABLE 1

| Parameter | Range | Typical Value |
| --- | --- | --- |
| Output Current | 0.1-6.0 mamp | 2.0 mamp |
| Pulse Width | 10-1500 μsec | 500 μsec |
| Frequency | 0.5-250 Hz | 150 Hz |
| On-time | 1 sec-unlimited | 30 sec |
| Off-time | 0 sec-unlimited | 300 sec |
| Frequency Sweep | 10-100 Hz | Optional |
| Random Frequency | 10-100 Hz | Optional |

On-time and off-time parameters are used to define an intermittent pattern in which a repeating series of pulses is generated for stimulating the nerve during the on-time (such a sequence is referred to as a "pulse burst"), followed by a period in which no pulses are generated, and the nerve is allowed to recover or rest from the stimulation provided by the pulse burst. The on/off duty cycle of these alternating periods of stimulation and no stimulation preferably has a ratio in which the off time may be set to zero, providing continuous stimulation, or may be as long as one day or more, in which case the stimulation is provided once per day or at even longer intervals. Typically, however, the ratio of the off-time to on-time ranges from approximately 0.5 to 10, i.e., the off-time is from half as long as the on-time to ten times the length of the on-time.

Nominally, the width of each pulse is set to a value not greater than about 1 millisecond, more typically 250-500 microseconds, and the pulse repetition frequency may programmed to be in a range of about 20 to 250 Hz. In one embodiment, a frequency of 150 Hz is used. A nonuniform frequency may also prove advantageous in minimizing addictive cravings. Frequency may be altered during a pulse burst by either a frequency sweep from a low frequency to a higher frequency or vice versa. Alternatively, the timing between adjacent individual pulses with in a burst may be randomly changed such that two adjacent pulses may be generated at any frequency within a range of frequencies. The electrical and timing parameters of the stimulating signal used for VNS as described herein for the preferred embodiment will be understood to be merely exemplary and not as constituting limitations on the scope of the invention, except insofar as recited in the claims.

Also, as shown in FIG. 2B, dual implanted NCP devices 10a and 10b may be used as the pulse generators, one attached to the right vagus and the other the left vagus to provide the bilateral stimulation. While the pulse generators 10a and 10b may be programmed with the same stimulation parameters, different stimulation parameters may also be effective in treating addiction disorders. Use of implanted stimulators for performing the methods of the invention is preferred, but treatment may conceivably be administered using an external stimulator with an internally implanted lead and electrode that are inductively coupled to the external stimulator, as suggested in U.S. Pat. No. 4,867,164 (FIG. 2). Wholly external stimulation may also be used on an out-patient basis, particularly where the cranial nerve stimulated is the trigeminal or glossopharyngeal nerves. Implantation of at least the electrode and the lead is preferred where vagus nerve stimulation is employed, because of the much greater efficiency provided by a direct electrical coupling. Moreover, implantation of one or more neurostimulators, of course, allows the patient to be completely ambulatory during treatment, so that normal daily routine activities are unaffected.

Another activation modality for stimulation is to program the output of the neurostimulator to the maximum amplitude which the patient can tolerate, with cycling on and off for a predetermined period of time followed by a relatively long interval without stimulation. Where the cranial nerve stimulation system is completely external to the patient's body, much higher current amplitudes much be employed to overcome the attenuation resulting from the absence of a direct contact with the vagus nerve and the additional impedance of the skin of the patient. While external systems will require much greater power consumption, the fact that batteries may be easily replaced without surgery may make external systems attractive.

The external stimulation may be used as a screening test to determine if the patient should receive an implanted cranial nerve stimulation system. In one embodiment, the invention comprises stimulating the trigeminal and/or glossopharyngeal nerve with a skin-mounted electrode to determine if the patient is responsive to cranial nerve stimulation for alleviating one or more symptoms of the substance addiction. In a particular embodiment, an electrode is coupled to the skin of the patient's cheek or temple to stimulate a trigeminal nerve. A lead connects the skin electrode to an electrical pulse generator carried by the patient, e.g., in a pocket or mounted on a belt. The patient is subjected to relatively high stimulation for a first test period to determine whether the patient's substance addiction is amenable to treatment with cranial nerve stimulation. The symptoms of the patient are analyzed following the first test period, and a decision is made whether or not implantation of an implantable system is warranted. If one or more symptoms of the patient are alleviated, the patient may be considered for an implanted system providing direct coupling to a cranial nerve. In certain embodiments, both external stimulation (providing an indirect contact, preferably with a trigeminal or a glossopharyngeal nerve) and internal stimulation (providing a direct contact, preferably with a vagus nerve) may be employed to alleviate a symptom of the substance addiction.

Other types of indirect stimulation may also be provided in certain embodiments of the invention. In one alternative embodiment, the invention comprises providing noninvasive TMS to the brain of the patient to alleviate symptoms of the substance addiction. Transcranial magnetic stimulation systems known in the art such as those disclosed in U.S. Pat. Nos. 5,769,778 and 6,132,361 (for treatment of psychiatric disorders) and U.S. Pat. No. 6,425,852 may be used to provide the treatment. Where TMS is used, it is preferably used in conjunction with cranial nerve stimulation as an adjunctive therapy. In some embodiments, TMS alone may be used to treat the substance addiction. In a particularly preferred alternative embodiment, TMS and direct vagus nerve stimulation are both provided to the patient to alleviate the substance addiction.

Returning to systems for providing direct cranial nerve stimulation, such as those in FIGS. 1, 2A-2C, and 3, stimulation may be provided in at least two different modalities. Where cranial nerve stimulation is provided based solely on programmed off-times and on-times (which may also be used to provide stimulation according to circadian rhythms), the stimulation is referred to as passive, inactive, or non-feedback stimulation. In contrast, stimulation may be triggered by one or more feedback loops according to changes within the body or mind of the patient. Such stimulation is referred to as active or feedback loop stimulation. The most common form of feedback loop stimulation is manually triggered stimulation, in which the patient manually causes the activation of a stimulation pulse burst outside of the programmed on-time/off-time cycle. For example, if the patient senses an impending craving or a withdrawal symptom, the patient may manually activate the neurostimulator to stimulate the vagus nerve, thus substantially reducing or eliminating cravings or other withdrawal symptoms. The patient also may be allowed to alter the intensity of the signals applied to the vagus nerve within limits established by a physician. For example, the patient may alter the signal frequency, current, duty cycle or a combination thereof. In at least some embodiments, the neurostimulator should be programmed to generate the stimulus for a relatively long period of time in response to manual activation. The treatment is designed, in part, to increase the activity of the vagus nerve by which to ameliorate the patient's addiction and/or withdrawal symptoms.

Patient activation of the neurostimulator may involve use of an external control magnet for operating a reed switch in the implanted device, for example. Certain other techniques of manual and automatic activation of implantable medical devices are disclosed in U.S. Pat. No. 5,304,206 to R. G. Baker, Jr. et al. (referred to herein as "the '206 patent"), which is assigned to the same assignee as the present application. According to the '206 patent, means for manually activating or deactivating the stimulus generator may include a sensor such as a piezoelectric element 31 mounted to the inner surface of the generator case and adapted to detect light taps by the patient on the implant site. One or more taps applied in fast sequence to the skin above the location of the stimulus generator in the patient's body may be programmed into the device as the signal for activation of the generator, whereas two taps spaced apart by a slightly longer time gap is programmed as the signal for deactivation, for example. The therapy regimen performed by the implanted device(s) remains that which has been pre-programmed by means of the external programmer, according to the prescription of the patient's physician in concert with recommended programming techniques provided by the device manufacturer. In this way, the patient is given limited but convenient control over the device operation, to an extent which is determined by the program dictated and/or entered by the attending physician. The patient also may activate the neurostimulator using other suitable techniques and/or apparatuses.

Feedback stimulation systems other than manually initiated stimulation are also within the scope of the present invention. Referring to FIG. 3, a system for triggering the vagus nerve stimulation based on feedback from a body parameter is provided. A sensing lead 130 is coupled at a proximal end to header 140 along with the stimulation lead and electrode assemblies 60, 70. A sensor 140 is coupled to the distal end of sensing lead 130. Sensor 140 may comprise a temperature sensor, a blood parameter sensor, a heart parameter sensor, a brain parameter sensor, or a sensor for another body parameter. The sensor may also comprise a nerve sensor for sensing activity on a nerve such as the vagus nerve. Sensor 140 preferably senses a body parameter that corresponds to a symptom of the addiction, and more preferably to a craving for the substance to which the patient is addicted. If sense electrodes are to be utilized to detect onset of addiction symptoms (e.g., cravings or other withdrawal symptoms) being treated, a signal analysis circuit is preferably incorporated in the neurostimulator for processing an analyzing the signals from the sensor 140. Upon detection of the symptom of interest of the addiction being treated, the processed digital signal is supplied to a microprocessor in the neurostimulator device, to trigger application of the stimulating signal to the patient's vagus nerve. In alternative embodiments, the detection of a symptom of interest may trigger a stimulation program comprising different stimulation parameters from a passive stimulation program, such as having a higher current or a higher ratio of on-time to off-time.

The principles of the invention may be applicable to selected cranial nerves other than the vagus nerve, to achieve the desired results. Hence, although certain preferred methods and modes of treating and controlling substance and alcohol addictions through a regimen generally of cranial nerve and specifically vagus nerve stimulation, directly or indirectly at a cervical or near-diaphragmatic location have been described herein, it will be appreciated by persons of ordinary skill in the art of nerve stimulation for treatment of addictions, diseases and disorders that variations and modifications may be made within the scope of the present invention as defined by the appended claims. All patents cited herein are hereby incorporated by reference in their entirety. It is therefore intended that the invention shall be limited only as required by the appended claims and by the rules of applicable law.

What is claimed is:

1. A method of treating a patient having a substance addiction, comprising:
   directly contacting an electrode to a vagus nerve of the patient, and applying an electrical signal to said electrode; and
   generating afferent action potentials on said vagus nerve to alleviate a symptom of the substance addiction,
   wherein the substance addiction is selected from the group consisting of cocaine addiction, alcoholism, addiction to opioids, sedative, hypnotic or anxiolytic-related disorders, hallucinogen related disorders, cannabis related disorders, amphetamine related disorders, nicotine related disorders, inhalant related disorders, phencyclidine related disorders, and polysubstance abuse disorders,
   wherein the symptom is a withdrawal symptom selected from the group consisting of nausea, vomiting, fever, dizziness, and profuse sweating.

* * * * *